(12) United States Patent
Takeshi et al.

(10) Patent No.: US 7,895,679 B2
(45) Date of Patent: Mar. 1, 2011

(54) GOGGLES

(75) Inventors: Katsuya Takeshi, Higashiosaka (JP);
Rintaro Inui, Higashiosaka (JP)

(73) Assignee: Yamamoto Kogaku Ltd., Higashiosaka-Shi, Osaka (JP)

(*) Notice: Subject to any disclaimer, the term of this patent is extended or adjusted under 35 U.S.C. 154(b) by 524 days.

(21) Appl. No.: 12/033,919

(22) Filed: Feb. 20, 2008

(65) Prior Publication Data
US 2008/0196149 A1 Aug. 21, 2008

(30) Foreign Application Priority Data
Feb. 20, 2007 (JP) ................. 2007-039361

(51) Int. Cl.
*A61F 9/02* (2006.01)
(52) U.S. Cl. .............................................. 2/448
(58) Field of Classification Search .............. 2/426, 431, 2/448, 439, 451
See application file for complete search history.

(56) References Cited

U.S. PATENT DOCUMENTS

| | | | |
|---|---|---|---|
| 6,047,410 A * | 4/2000 | Dondero | 2/426 |
| 6,076,196 A * | 6/2000 | Masumoto | 2/436 |
| 6,105,177 A | 8/2000 | Paulson et al. | |
| 6,732,383 B2 * | 5/2004 | Cleary et al. | 2/450 |
| 2003/0101507 A1 | 6/2003 | Cleary et al. | |
| 2005/0160521 A1 | 7/2005 | Hussey | |
| 2005/0264753 A1 * | 12/2005 | Hartley et al. | 351/83 |
| 2007/0153230 A1 * | 7/2007 | Musal et al. | 351/142 |

FOREIGN PATENT DOCUMENTS

| | | |
|---|---|---|
| EP | 1702596 | 9/2006 |
| JP | 10229998 | 2/1998 |
| WO | 2007084255 | 7/2007 |

OTHER PUBLICATIONS

European Search Report EP08003139.

* cited by examiner

*Primary Examiner* — Katherine Moran
(74) *Attorney, Agent, or Firm* — Heslin Rothenberg Farley & Mesiti P.C.

(57) ABSTRACT

Goggles include a lens frame and connection arms for a wearing belt. The connection arms are provided respectively at right and left parts on a side of a front surface of the lens frame. Each of the connection arms is selectively kept in a state that the arm overlaps and rests on the front surface of the lens frame, or in a state that the arm stays at a position with a space from the front surface of the lens frame after having moved rotationally on its inner end from the front surface of the lens frame outwardly. The goggles provide a preferable fitted comfortability to a wearer's face regardless of whether he uses a helmet or not and regardless of the thickness of the inner liner of the helmet.

18 Claims, 17 Drawing Sheets

GOGGLES

TECHNICAL FIELD OF THE INVENTION

The present invention relates to goggles that a user can use in either case of wearing a helmet or not.

BACKGROUND OF THE INVENTION

A user sometimes wears goggles on a helmet in case of sport such as skiing and work such as electric work, civil work and the like which require a helmet. In a ski competition, whether wearing a helmet or not mainly depends on sliding speeds of various races.

Conventional goggles which a user wears on a helmet require a different design from those a user wears directly on his head. In case a user wears a helmet, the thickness of an interior part or a shell of the helmet changes the direction of force of a wearing belt which is applied on the goggles, which sometimes resulting in deteriorating the fitted comfortability of the goggles to the user's face and inducing the invasion of wind and snow into the inside of the goggles.

In the design for conventional goggles adjusted for a helmet is seen a trend that a lens frame 21 is rather wide laterally in a front view and has a large thickness, as shown in FIG. 12. This is because that the frame of the goggles is designed to match with the thickness of the helmet. Due to this large thickness, when a user wears the goggles directly on his head, the goggles give less fitted comfortability to his face than general goggles not designed for use on a helmet. In FIG. 12, numeral 22 denotes a wearing belt, character R denotes an interior liner, and character M denotes a head of a person.

In addition, when conventional general goggles designed not for a helmet are put on a helmet, a rising force from a wearer's face is likely to be generated on the goggles by tensile force of the wearing belt 22. This is because a connection position of the wearing belt 22 comes to lie between a helmet surface and a wearer's face due to the smaller thickness of the right and left parts of the lens frame 21. As shown in FIG. 13, although there are some goggles in which a connection position between a wearing belt 22 and a lens frame 21 comes to lie closer to the helmet surface by means of another part P, the direction of the force of the wearing belt 22 doesn't change much, and presently only a small effect is recognized.

It is noted from the above that, if contestants play in plural races, especially in severe sports in which the fitted comfortability of the goggles to their faces and the functions of them are crucial factors and directly affect the results, the contestants must have plural pairs of goggles suitable for helmets depending on respective races.

The goggles described above are for skiing. Since goggles for motocross, goggles for other sports, and goggles for various kinds of work are also required fitted comfortability to a wearer's face, they have the same problem.

Thus, goggles that can give a wearer a suitable fitted comfortability to his face regardless of whether a helmet is used or not, and regardless of the thickness of an interior liner of the helmet have been provided.

One example is shown in FIG. 14. The goggles include arms 23 of soft-type elastic synthetic resin which are formed as one body with a lens frame 21 and project from the projecting positions on the right and left parts of the upper and lower parts of the lens frame 21. Each of the arms 23 has an end in the vicinity of a belt coupling position apart from the above projecting position, and connected to a stretch elastic belt 25 in the vicinity of that end through a belt connecting part 24. Thus, the arm 23 is elastically deformed to overlap with at least one part of a front surface of the lens frame 21, or to roughly extend along and in front of the front surface. One of the specific examples of such goggles is shown in Japanese Unexamined Patent Publication No. 10-229998 (page 2, FIGS. 1, 5, 7 and 8).

The goggles with the above structure are shown in FIG. 15. It is described that when a user wears the goggles on a helmet with a thin interior liner R, the restoring force of the stretch elastic belt 25 is converted to a pressure of the goggles to the wearer's face, the force rising from the wearer's face is not generated. It is also described that, as shown in FIG. 16, when a user wears the goggles on a helmet with a thick interior liner R, the force rising from the user's face is not generated, either. Further it is described that as shown in FIG. 17, when the goggles are put on directly on a person's head M, due to the restoring force of the stretch elastic belt 25, the front face of the lens frame 21 and an inner face of the arm 23 come to closer or in contact with each other, and the pressure toward to the person's face is applied, so that the rising force where the goggles are lifted apart from the person's face will not work.

However, in the foregoing conventional goggles, as shown in FIG. 16, when the helmet having the thick interior liner R is used, the arms 23 are elastically deformed toward the lens frame 21, and an outer end of each of the arms 23 sometimes abuts on an opening end 26 of the thick interior liner R. In such a case, the arms 23 is bounced back by the interior liner R and the force in which the goggles are lifted up from a wearer's face may be caused and then such goggles cannot provide a fitted comfortability to a wearer's face.

SUMMARY OF THE INVENTION

It is hence an object according to the present invention to solve the above conventional problems, in particularly to provide goggles that can provide a fitted comfortability to a wearer's face regardless of whether a helmet is used or not and regardless of whether an interior liner of the helmet is thick or thin.

Goggles according to the present invention include connection arms of a wearing belt on a side of a front surface of right and left parts of a lens frame. The connection arms are kept selectively in one of states that each of the arms overlaps and rests on the front surface of the lens frame and that each of the connection arms stays at a position with a space from the front surface of the lens frame after having moved rotationally on its inner end from the front surface of the lens frame outwardly.

The goggles according to the present invention further include a pivot hole, an engagement hole and an abutment part on each of upper and lower parts on the side of the front surface of the right and left parts of the lens frame, and a pivot part, an engagement part and an abutting part on an inner end part of each of the connection arms. The pivot part of the connection arm is pivotally supported in the pivot hole of the lens frame, and the engagement part of the connection arm is engaged with the engagement hole of the lens frame, so as to keep each of the connection arms overlapping and resting on the front surface of the lens frame.

In the goggles stated above, the pivot part of the connection arm is pivotally supported in the pivot hole of the lens frame, the engagement part of the connection arm is engaged with the front surface of the lens frame, and furthermore the abutting part of the connection arm touches the abutment part of the lens frame to be positioned there. Thus each of the connection arms is kept staying there with a space from the front surface of the lens frame after having moved rotationally on its inner end part from the front surface of the lens frame outwardly.

The goggles according to the present invention may include a pivot part, an engagement hole and an abutment part on each of upper and lower parts on a side of a front surface of right and left parts of a lens frame, and a pivot hole, an engagement part and an abutting part on an inner end part of the each of the connection arms. The pivot hole of the connection arm pivotally supports the pivot part of the lens frame, and the engagement part of the connection arm is engaged with the engagement hole of the lens frame, so that each of the connection arms is kept in a state in which the connection arm overlaps and rests on the front surface of the lens frame. Alternatively, the pivot hole of the connection arm pivotally supports the pivot part of the lens frame, the engagement part of the connection arm engages with the front surface of the lens frame, and further the abutting part of the connection arm touches the abutment part of the lens frame to be positioned there, so that each of the connection arms is kept in a state in which the connection arm stays there with a space from the front surface of the lens frame after having moved rotationally on its inner end side from the side of the front surface of the lens frame outwardly.

Furthermore, in the goggles according to the present invention, the pivot hole of the lens frame penetrates the lens frame, and a tip end of the pivot part of the connection arm is provided with a retaining part to prevent removal from the pivot hole.

In addition, in the goggles according to the present invention, the pivot hole of the connection arm may penetrate the connection arm, and a tip end of the pivot part of the lens frame is provided with a retaining part to prevent removal from the pivot hole.

Furthermore, in the goggles according to in the present invention, the pivot hole and the engagement hole of the lens frame are provided in a recess part formed on each of the upper and lower parts of the right and left parts of the lens frame, and the recess part receives the inner end part of the connection arm.

Furthermore, according to the goggles in the present invention, the pivot part and the engagement hole of the lens frame may be provided in a recess part which is formed on each of the upper and lower parts of the right and left parts of the lens frame and receives the inner end part of the connection arm.

Furthermore, in the goggles according to the present invention, the connection arms protrude out from the right and left parts of the lens frame.

Furthermore, in the goggles according to the present invention, each of the connection arms has a rotational angle of a range of 15 to 22 degrees in which the connection arm moves rotationally on its inner end side from the front surface of the lens frame outwardly.

Furthermore, the lens frame of the goggles according to the present invention is formed of soft-type elastic synthetic resin and the connection arms are formed of hard-type elastic synthetic resin.

With the constitution stated above, the goggles of the present invention provide a preferable fitted comfortability to a wear's face regardless of whether a helmet is used or not and regardless of the thickness of an interior liner of a helmet.

DETAILED DESCRIPTION OF THE PREFERRED EMBODIMENTS

Figure 1:
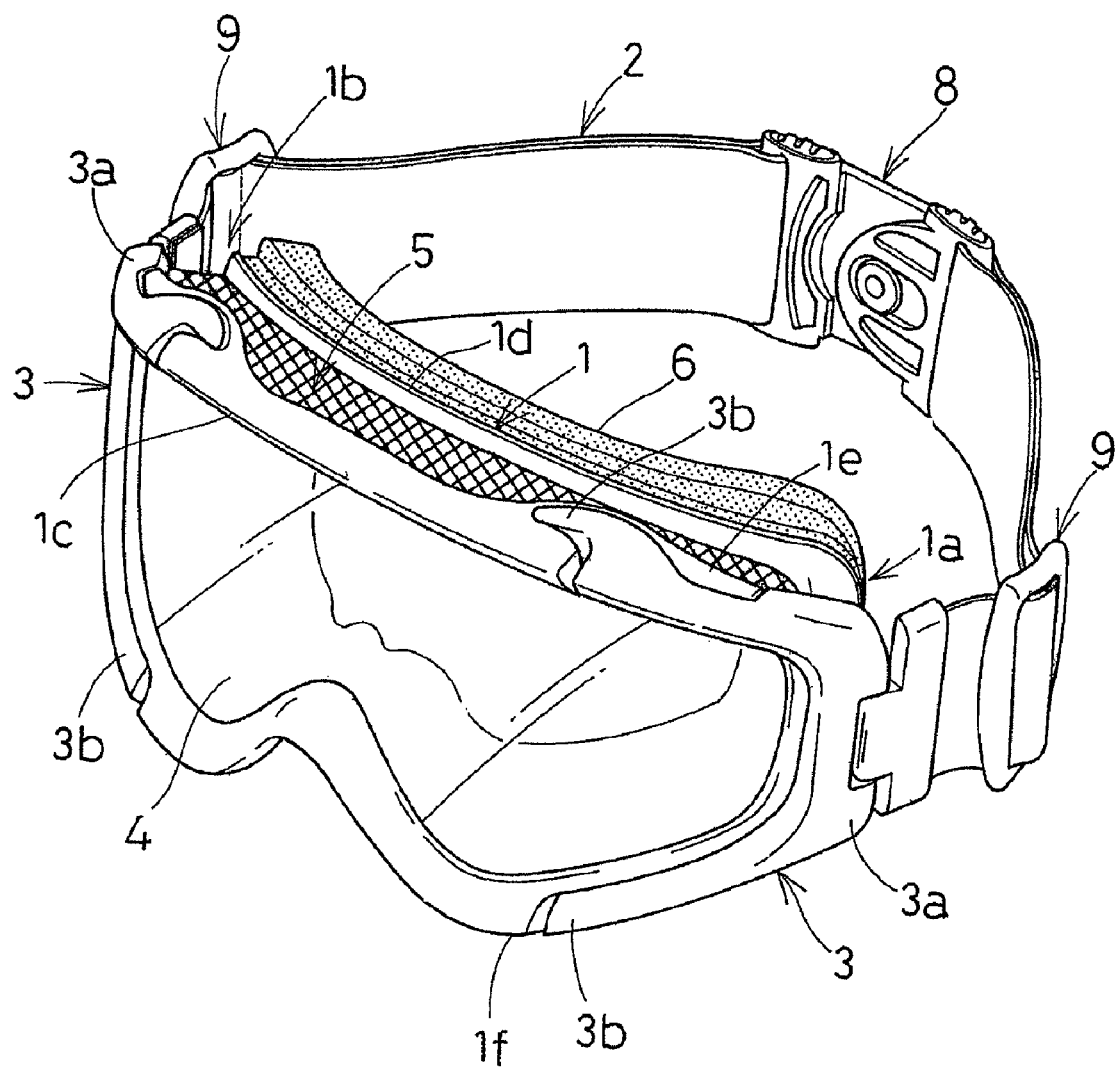
FIG. 1 is an overall perspective view of goggles according to one embodiment of the present invention showing a state that each of connection arms overlaps and rests on a front surface of a lens frame.

The preferred embodiments for carrying out goggles of the present invention will be described in detail with reference to the drawings hereinafter.

FIGS. 1 to 7 show one embodiment of the goggles of the present invention. Connection arms 3 for a wearing belt 2 are detachably mounted on parts of a front surface 1c of right and left parts 1a and 1b of a lens frame 1.

The lens frame 1 is detachably or fixedly provided with a lens 4 made of an acrylic resin plate and the like, and has a ventilation part 5 on an upper part and/or other appropriate parts so as to prevent the lens 4 from fogging. The lens frame 1 is formed of soft-type elastic synthetic resin such as urethane resin. Also, the lens frame 1 is provided with a sponge pad 6 on the side of a rear surface 1d (the side to be in contact with a wearer's face). In addition, the ventilation part 5 is covered with a cloth 7 or the like made of a water-repellent mesh fabric so as to prevent snow or dust and the like from entering the inside of the goggles.

The wearing belt 2 is made up with two detachable parts through a buckle 8 at the center of the belt, and both end parts of the belt are connected to respective outer end parts 3a of the connection arms 3. Furthermore, length adjusters 9 are mounted on near the both end parts of the belt. In addition, the wearing belt 2 is preferably an elastic belt, but not limitative thereto, and it may be a non-elastic one.

Figure 5:
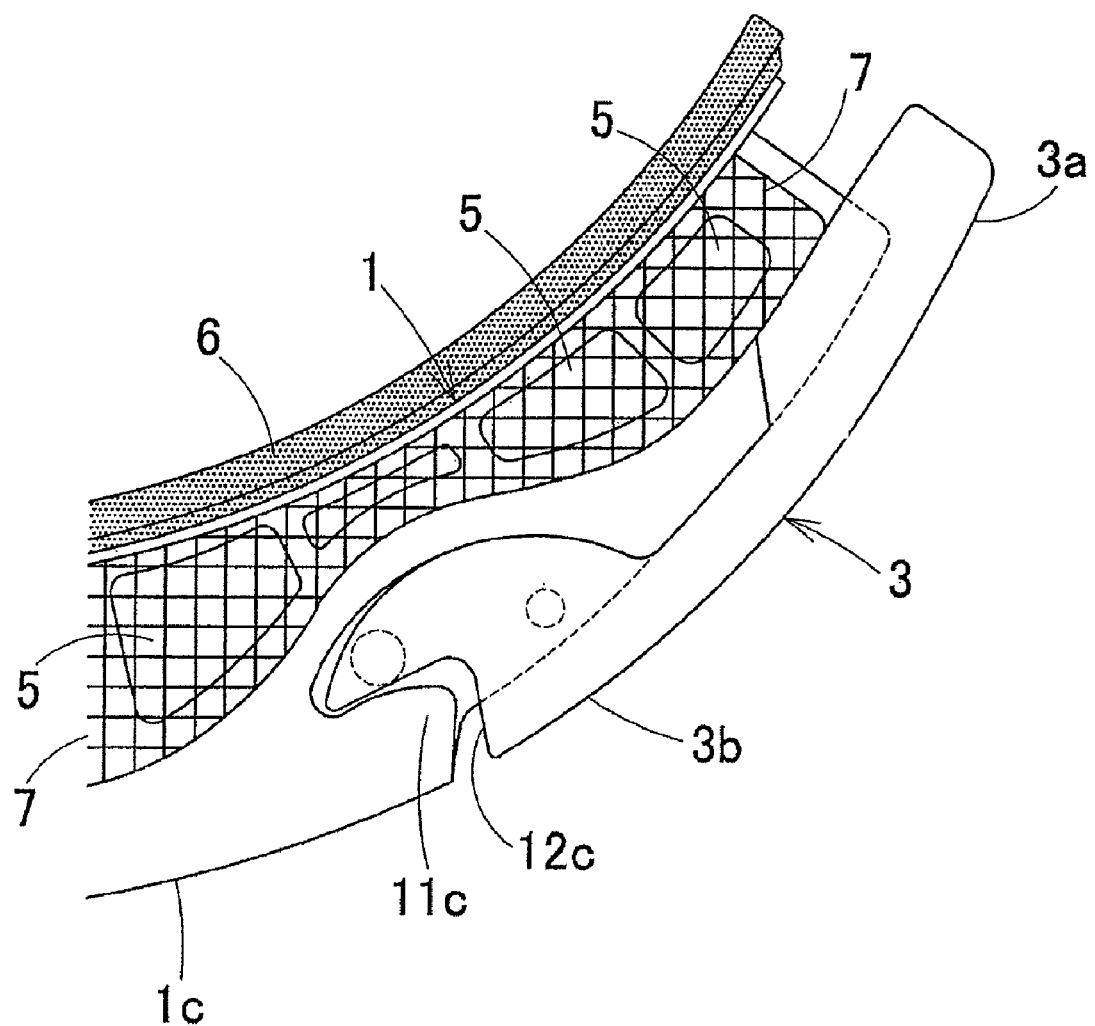
FIG. 5 is a plan view showing the state in which the connection arm overlaps and rests on a front surface of a lens frame.
Figure 7:
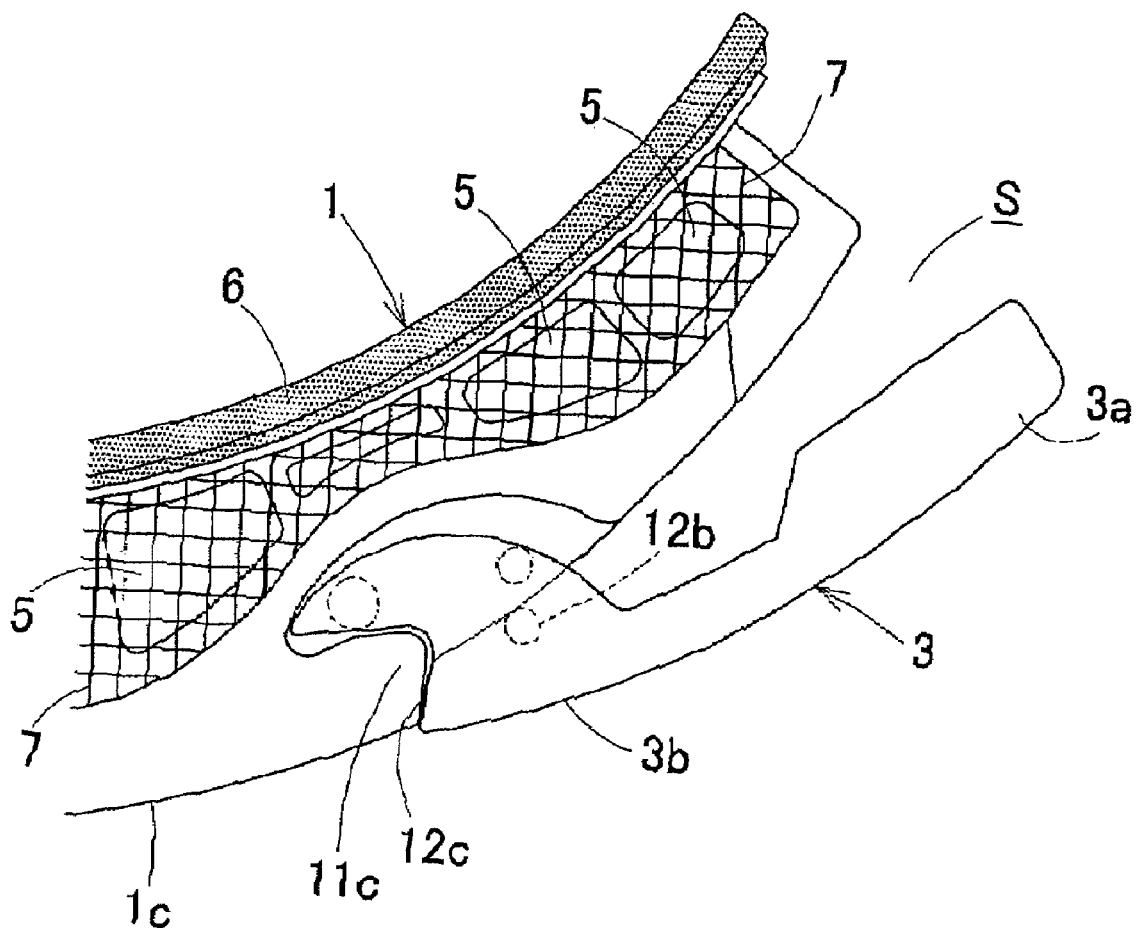
FIG. 7 is a plan view showing a state in which, after having moved rotationally on the inner end part from the front surface of the lens frame outwardly, the connection arm stays there having a space from the front surface.

The connection arms 3 preferably have configurations corresponding to respective shapes of the right and left parts 1a and 1b of the lens frame 1. In the drawings, each of the arms has a roughly U-shaped configuration in which upper part and lower part continue in one body, but the arm may be made up with an upper part and a lower part separately. As long as the connection arms 3 can be mounted on the side of the front surface 1c of the right and left parts 1a and 1b of the lens frame 1 and the wearing belt 2 can be connected therewith, the shape of the connection arm is not limitative. The connection arm 3 is formed of hard-type elastic synthetic resin such as an ABS resin, not to be easily deformed by bending. Each of the connection arms 3 can be kept selectively in either state that it overlaps and rests on the front surface 1c of the lens frame 1 as shown in FIG. 5, or that it stays at a position having a space S from the front surface 1c of the lens frame 1 after having moved rotationally on a side of an inner end 3b from the front surface 1c of the lens frame 1 outwardly as shown in FIG. 7. Changing the mode of the connection arm from the state in FIG. 5 to that in FIG. 7 requires removal of the connection arm 3 off the lens frame 1. Since the lens frame 1 is formed of soft-type elastic synthetic resin, the connection arm 3 can be moved off by elastically deforming the lens frame 1.

Figure 2:
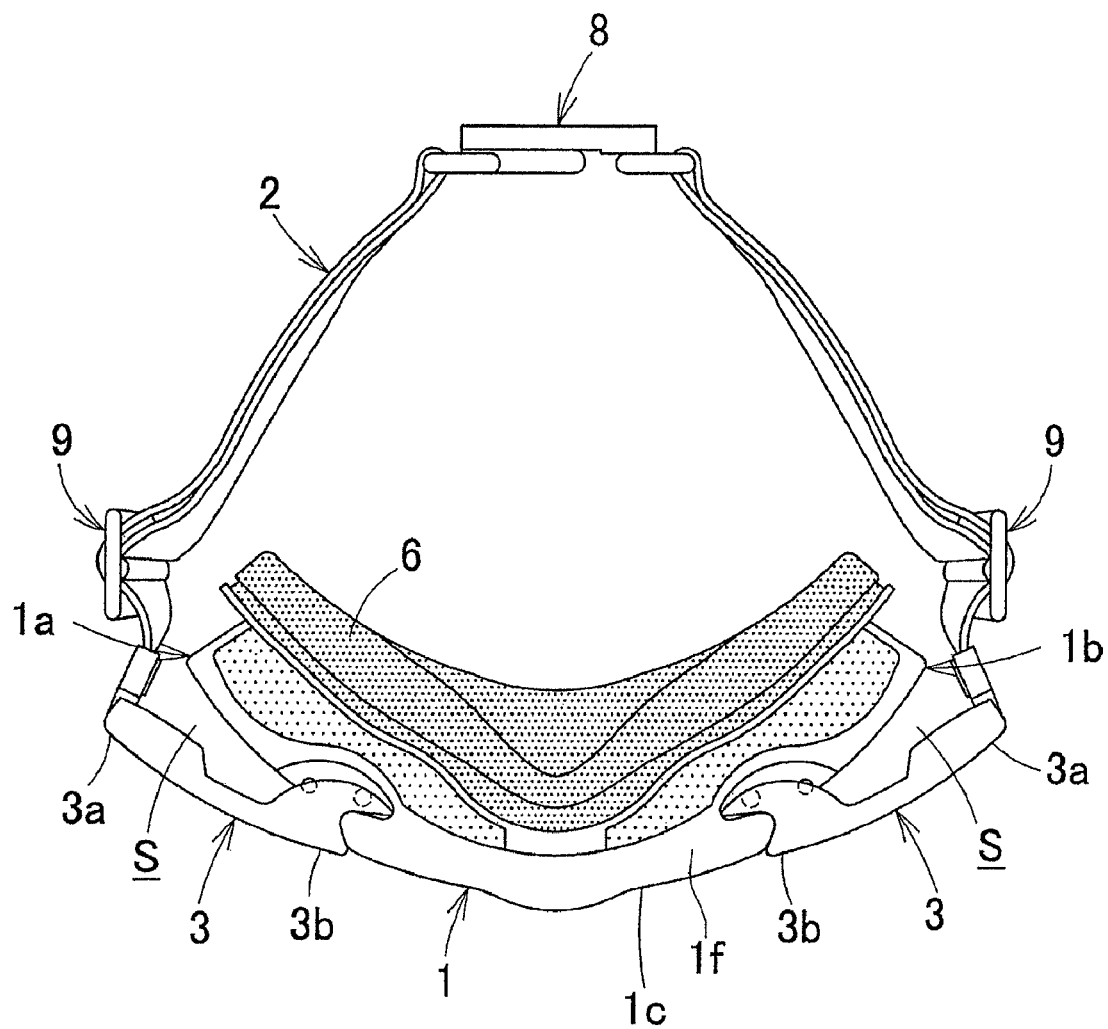
FIG. 2 is a bottom view showing a state that, after having moved rotationally on the inner end from the front surface of the lens frame outwardly, each of the connection arms of the present invention stays there having a space from the front surface.
Figure 3:
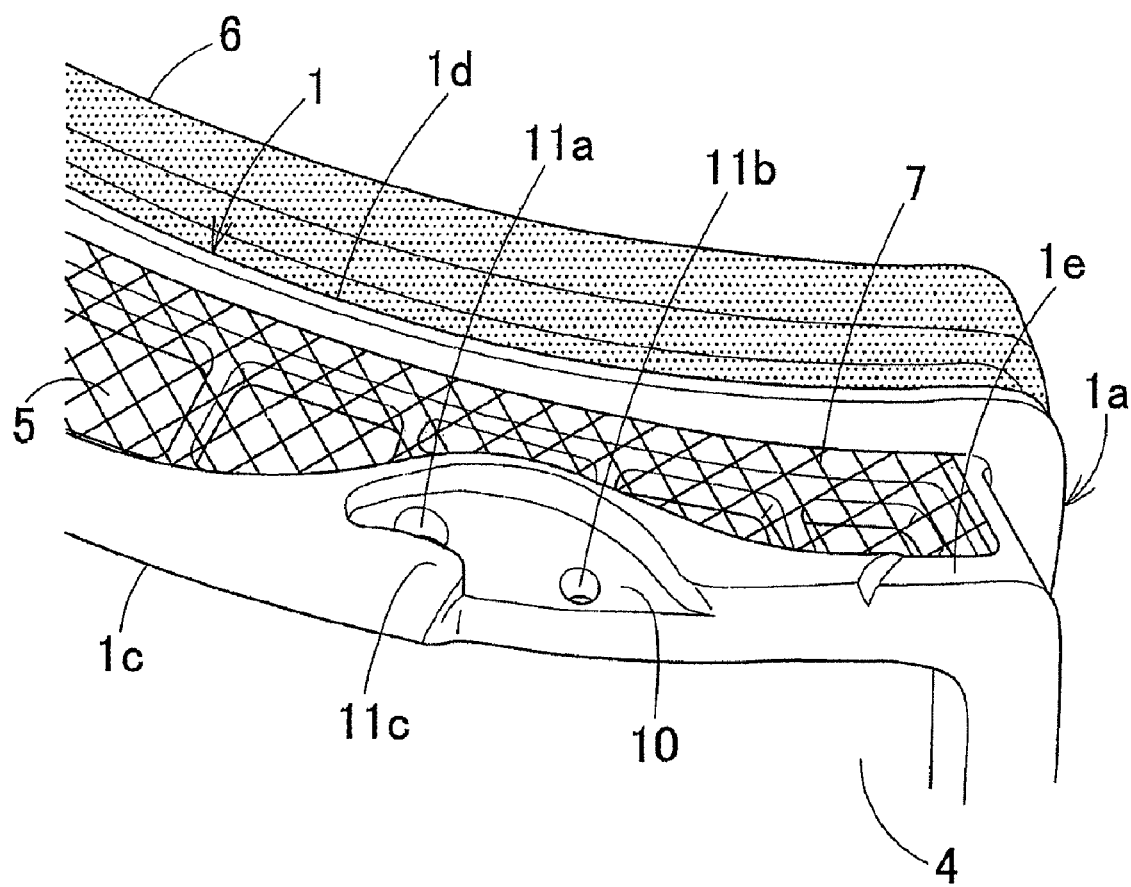
FIG. 3 is a partially enlarged view showing an upper end part of the lens frame of the goggles according to the present invention.
Figure 4:
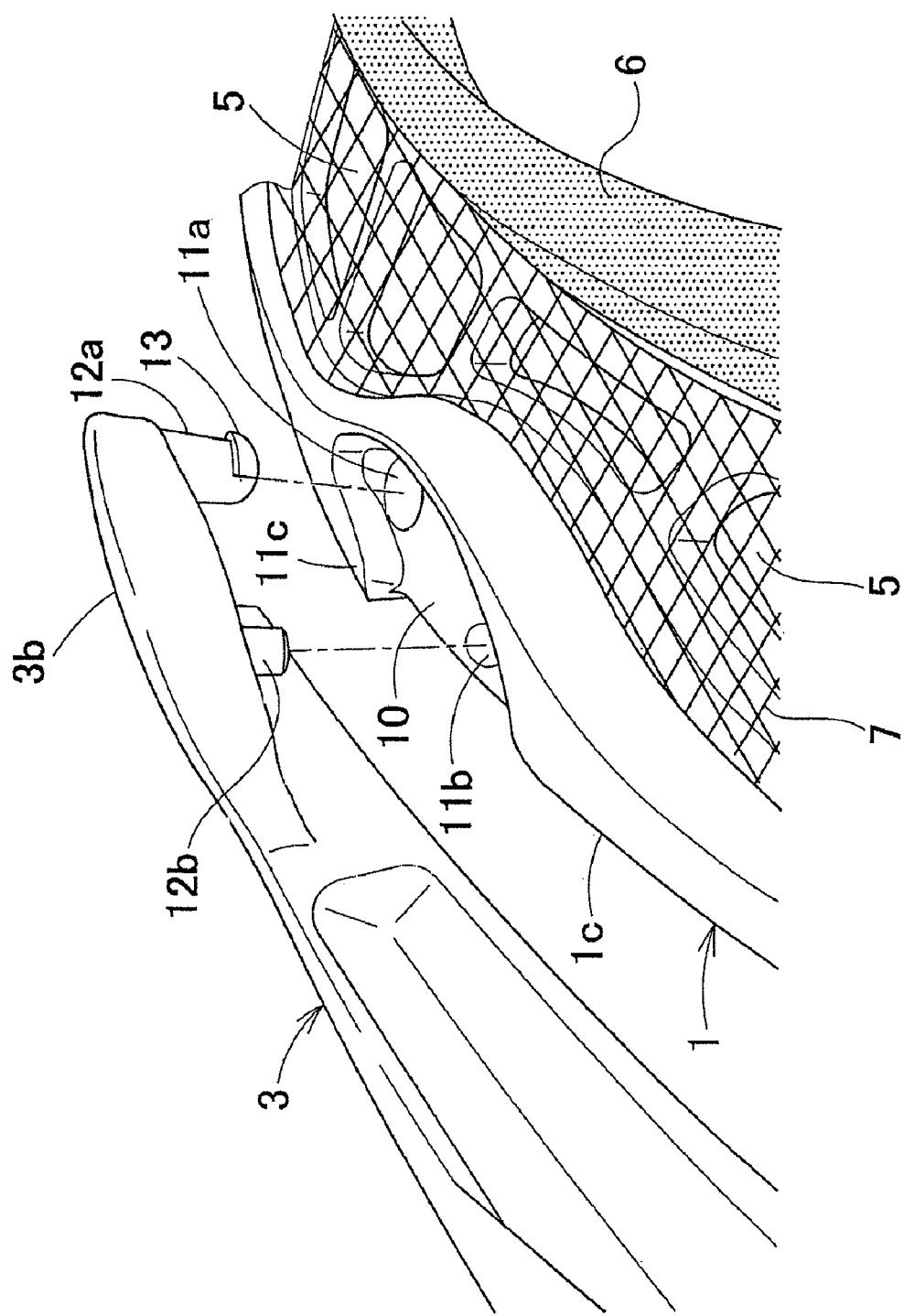
FIG. 4 is an explanatory view showing a way of coupling the connection arm and the lens frame of the goggles according to the present invention so that the former overlaps and rests on the front surface of the latter.

In the goggles according to the present invention, in order to keep each of the connection arms 3 overlapping and resting on the front surface 1c of the lens frame 1, upper part and lower part 1e and 1f on the side of the front surface 1c of the left and the right parts 1a and 1b of the lens frame 1 (as shown in FIGS. 1 and 2) are respectively provided with a pivot hole 11a, an engagement hole 11b and an abutment part 11c, as shown in FIGS. 4 and 5. And the inner end part 3b of the connection arm 3 is provided with a pivot part 12a for the pivot hole 11a, an engagement part 12b for the engagement hole 11b, and an abutting part 12c for the abutment part 11c. Thus, as shown in FIG. 4, the pivot part 12a of the connection arm 3 is engaged with the pivot hole 11a of the lens frame 1 and the engagement part 12b of the connection arm 3 is engaged with the engagement hole 11b of the lens frame 1.

Figure 6:
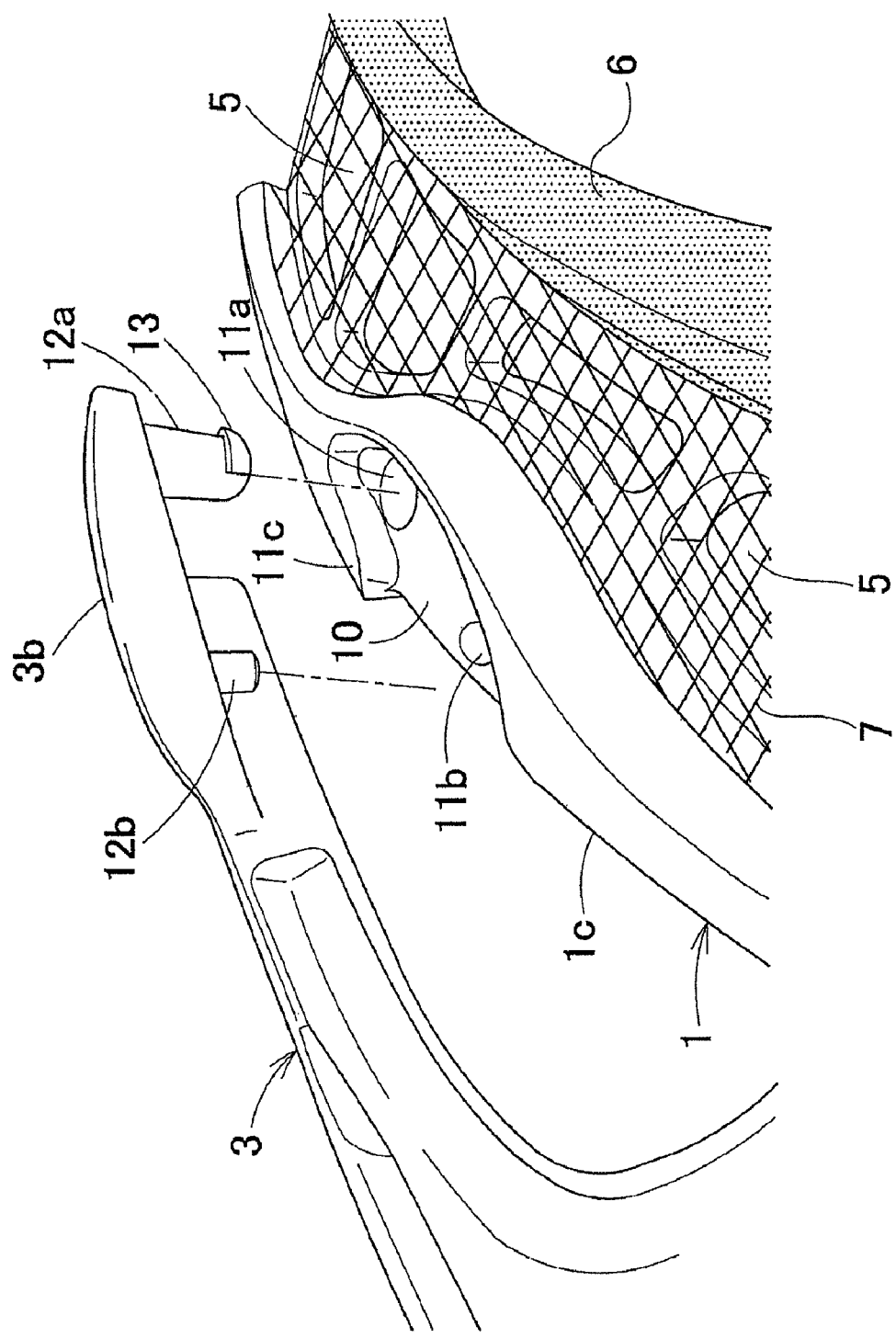
FIG. 6 is an explanatory view showing a way of coupling the connection arm and the lens frame of the goggles according to the present invention so that the former moves rotationally on the inner end part from the front surface of the latter outwardly to stay having a space from the front surface.

Furthermore, in the goggles according to the present invention, in order to keep each of the connection arms 3 staying at a position with a space S from the front surface 1c after having moved rotationally on the inner end part 3b from the front surface 1c of the lens frame 1 outwardly, as shown in FIGS. 6 and 7, the pivot part 12a of the connection arm 3 is engaged with the pivot hole 11a of the lens frame 1, the engagement part 12b of the connection arm 3 is engaged with the front surface 1c of the lens frame 1, and the abutment part 12c of the connection arm 3 abuts on the abutment part 11c of the lens frame 1.

In addition, the pivot hole 11a of the lens frame 1 penetrates the lens frame 1 and a tip end of the pivot part 12a of the connection arm 3 is provided with a retaining part 13 with respect to the pivot hole 11a. This prevents the connection arm 3 from removing from the lens frame 1 and facilitates reliable coupling between the connection arm 3 and the lens frame 1. The abutment part 11c of the lens frame 1 has a convex shape while the abutting part 12c of the connection arm 3 has a concave shape, but not limitative thereto and they may be shaped reversely.

The pivot hole 11a and the engagement hole 11b of the lens frame 1 are formed in a recess part 10 provided each on at the upper and lower parts 1e and 1f of the right and left parts 1a and 1b of the lens frame 1 and the recess part 10 receives the inner end part 3b of the connection arm 3. With this structure, each of the connection arms 3 does not protrude from the upper and lower parts 1e and 1f of the right and left parts 1a and 1b of the lens frame 1 but flushes with the upper and lower parts 1e and 1f. The connection arm 3 does not stand as an obstacle and thereby air resistance becomes low. Therefore, the goggles according to the present invention become suitable for goggles for various types of work as well as sporting goggles.

Figure 8:
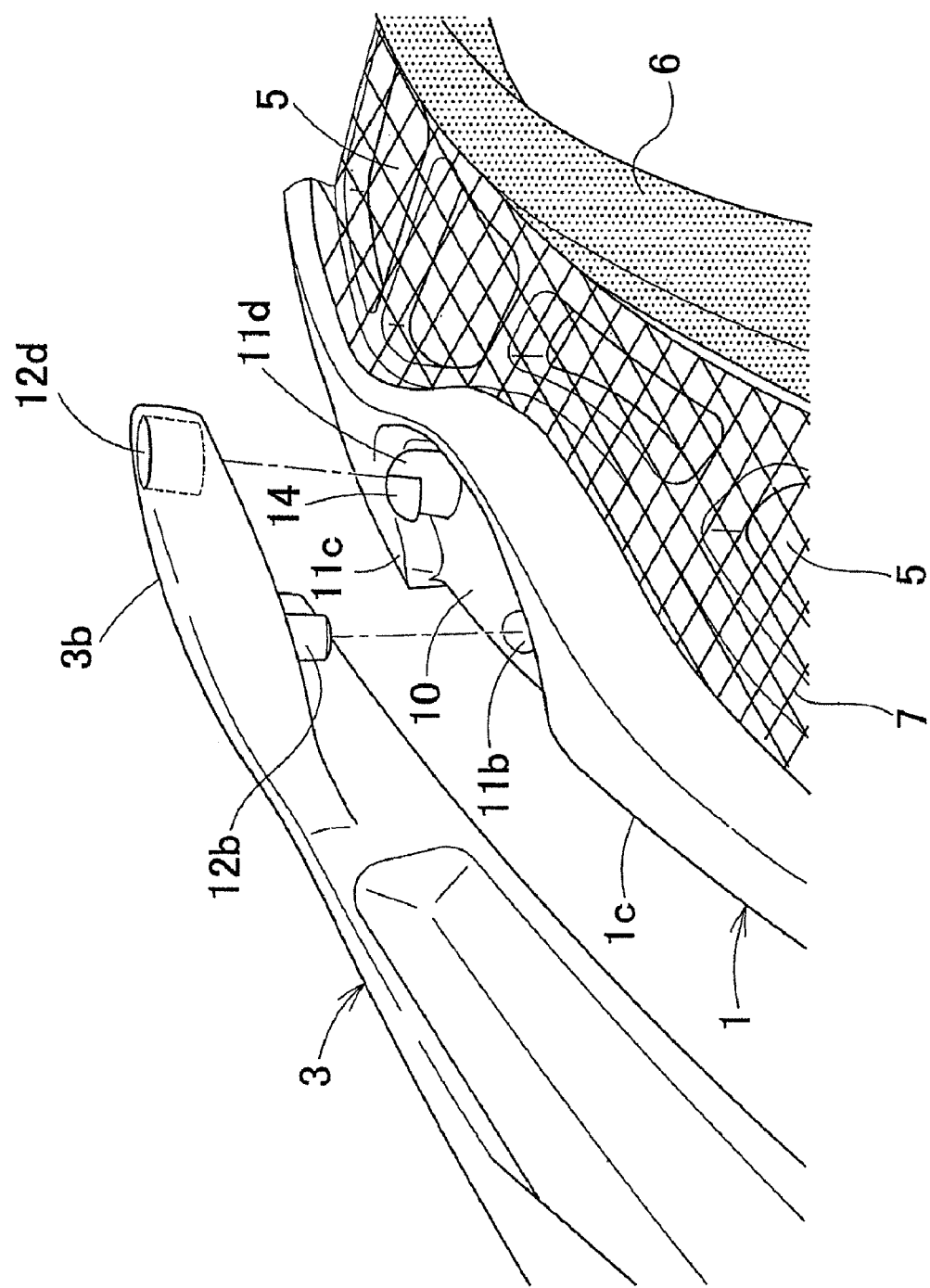
FIG. 8 is an explanatory view showing a way of coupling the connection arm and the lens frame of the goggles according to another embodiment of the present invention so that the former overlaps and rests on the front surface of the latter.

In addition, in the goggles according to the present invention, the mode that the connection arm 3 is needed to be kept in a state in which it overlaps and rests on the front surface 1c of the lens frame 1 is shown in FIG. 8. Each of the upper and lower parts 1e and 1f on the side of the front surface 1c of the right and left parts 1a and 1b of the lens frame 1 is provided with the pivot part 11d, the engagement hole 11b and the abutment part 11c, and the inner end part 3b of each of the connection arms 3 is provided with the pivot hole 12d for the pivot part 11d, an engagement part 12b for the engagement hole 11b, and an abutting part 12c for the abutment part 11c. Thus, the pivot hole 12d of the connection arm 3 is engaged with the pivot part 11d of the lens frame 1 and the engagement part 12b of the connection arm 3 is engaged with the engagement hole 11b of the lens frame 1.

Figure 9:
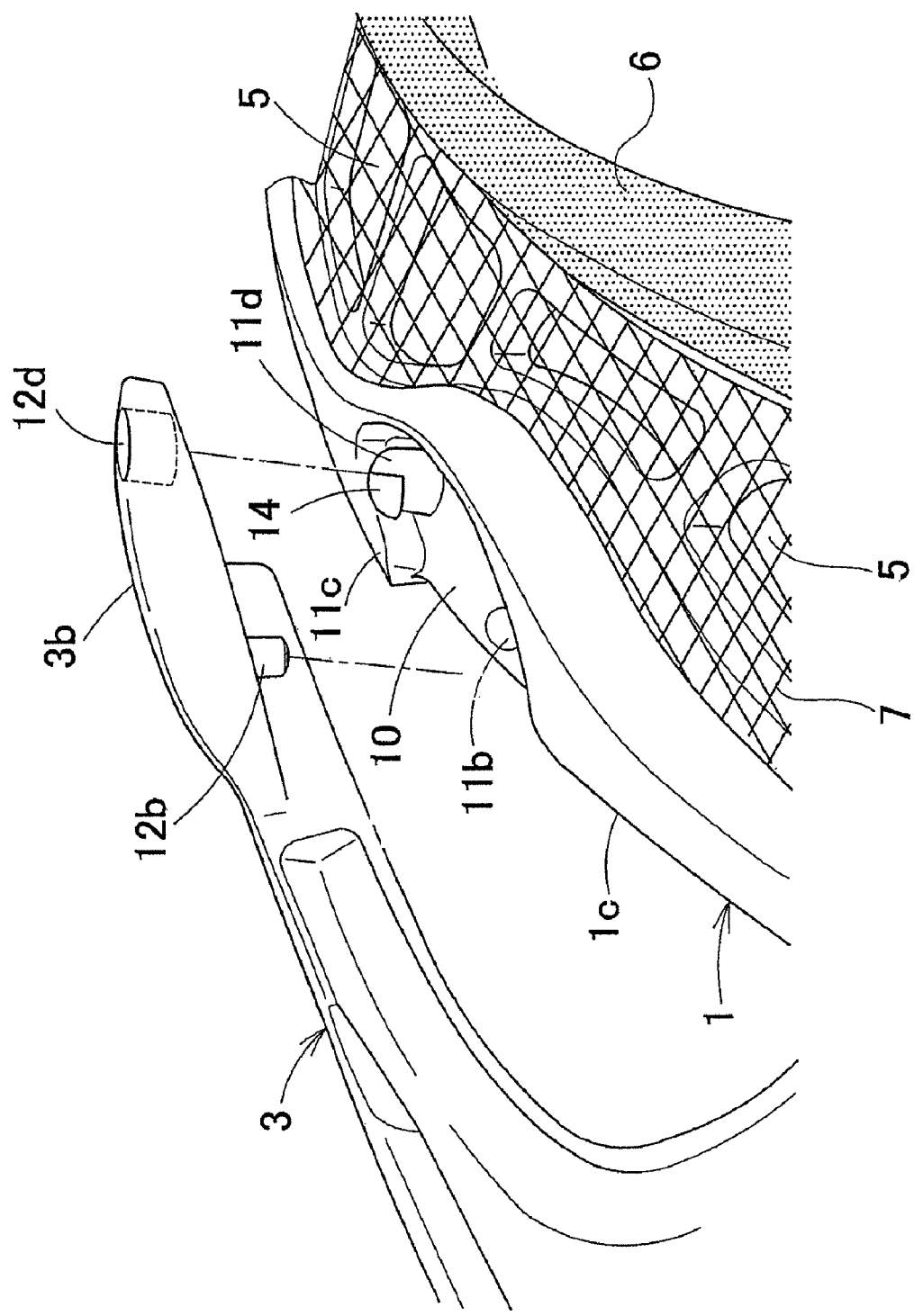
FIG. 9 is an explanatory view showing a way of coupling the connection arm of the lens frame of the goggles according to another embodiment of the present invention so that the former moves rotationally on the inner end part from the front surface of the latter outwardly to stay having a space from the front surface.

Furthermore, in the goggles according to the present invention, the mode that the connection arm 3 is needed to be maintained in a state in which, after having moved rotationally on the inner end part 3b from the front surface 1c of the lens frame 1 outwardly, the connection arm 3 stays at a position with a space S from the front surface 1, is shown in FIG. 9. The connection arm 3 is to be positioned where the pivot hole 12d of the connection arm 3 is engaged with the pivot part 11d of the lens frame 1, the engagement part 12b of the connection arm 3 abuts the front surface 1c of the lens frame 1, and the abutment part 12c of the connection arm 3 abuts the abutment part 11c of the lens frame 1.

The pivot hole 12d of the connection arm 3 penetrates the connection arm 3 and a tip end of the pivot part 11d of the lens frame 1 is provided with a retaining part 14 to be retained in the pivot hole 12d of the connection arm 3. Thus, the connection arm 3 is unlikely to remove off the lens frame 1, so that the connection arm 3 can be reliably mounted on the lens frame 1. In addition, as described above, the abutment part 11c of the lens frame 1 has a convex shape while the abutting part 12c of the connection arm 3 has a concave shape, but not limitative thereto and they may be shaped reversely.

Furthermore, the pivot parts 11d and the engagement holes 11b of the lens frame 1 are formed in the recess parts 10 formed respectively at the upper and lower parts 1e and 1f of the right and left parts 1a and 1b of the lens frame 1, and the recess parts 10 receives the inner end parts 3b of the connection arms. Thus, as stated above, the connection arms 3 do not protrude from the upper and lower parts 1e and 1f of the right and left parts 1a and 1b of the lens frame 1, but flush with the upper and lower parts 1e and 1f. As a result the connection arms 3 don't stand there as obstacles and air resistance becomes low. Therefore, the goggles can be preferably used as goggles for various types of work and for sports.

In addition, in the goggles according to the present invention, each of the outer end parts 3a of the connection arms 3 protrudes from the right and left parts 1a and 1b of the lens frame 1. Thus, the belt end parts connected to the outer end parts 3a of the connection arms 3 are prevented from abutting the lens frame 1 and being lifted up. Therefore, the connection arms 3 can be kept overlapping on the front surface 1c of the lens frame 1 without rising up and separating therefrom.

Furthermore, in the goggles according to the present invention, an angle wherein each of the connection arms 3 moves rotationally on the side of the inner end part 3b from the side of the front surface 1c of the lens frame 1 outwardly is set within a range of 15 to 22 degrees. A rotating angle smaller than 15 degrees is not preferable because, in the case where an inner liner R of a helmet is thick, the outer end part 3a of the connection arm 3 could abut on an opening end 15 of the inner liner R. On the other hand, a rotating angle larger than 22 degrees is not preferable, either, because the outer end part 3a of the connection arm 3 comes into view of a goggle wearer and narrows his sight.

In the goggles according to the present invention, when a rotational center of each of the connection arms 3 is set at a position provided by dividing the lens frame 1 lengthwise into three equal parts, tensile force of the connection arm 3 by the wearing belt 2 can be applied to the entire frame in balance, which provides a stable comfortability to a wearer.

In the goggles according to the present invention, the rotational angle of the connection arm 3 can be variously adjusted within the above range. This can be realized by providing a plurality of engagement holes 11b on the upper and lower parts 1e and 1f on the side of the front surface 1c of the right and left parts 1a and 1b of the lens frame 1.

Figure 10:
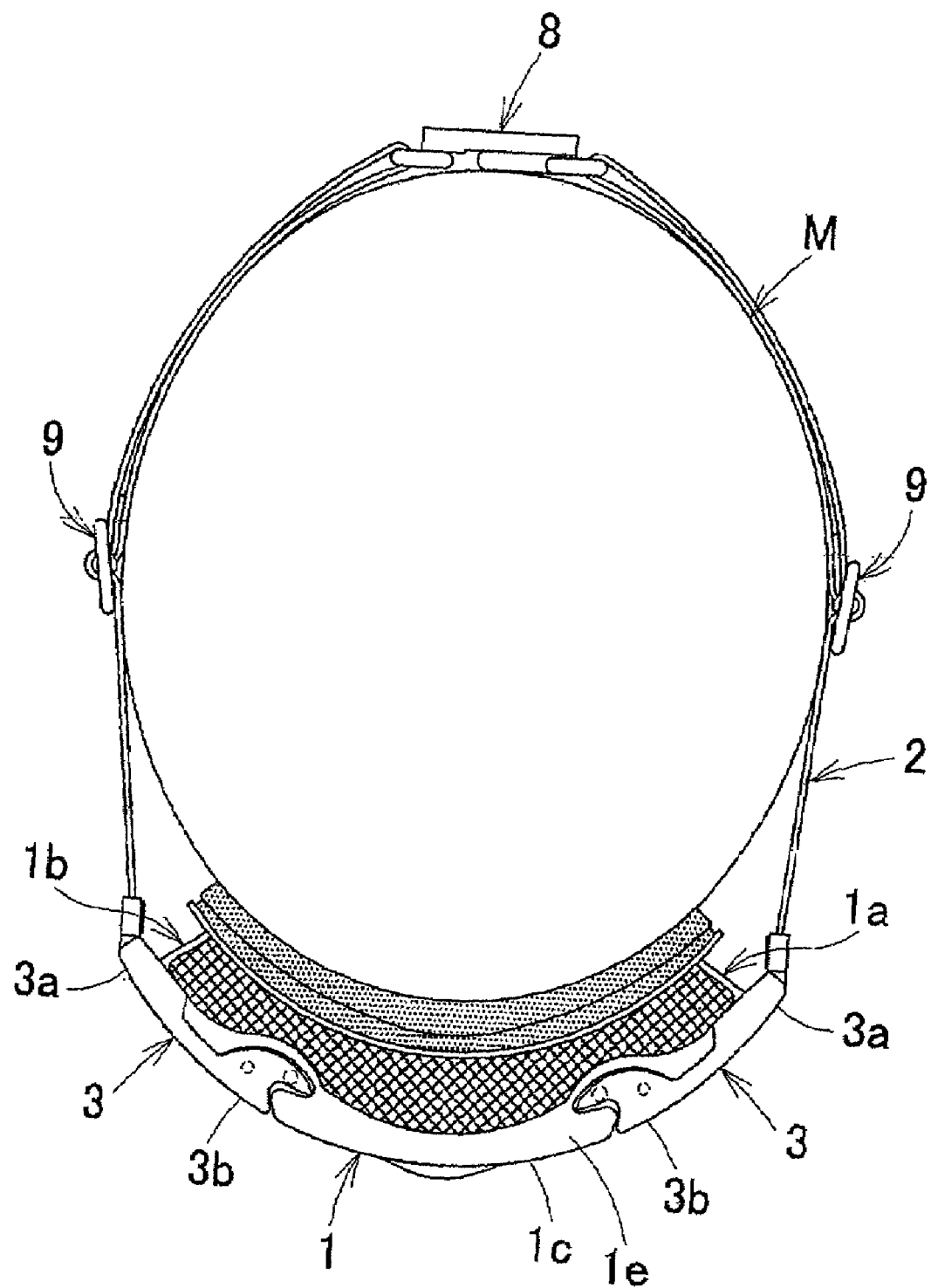
FIG. 10 is an explanatory view showing a state when the goggles of the present invention, in which the connection arms of the goggles are kept overlapping and resting on the front surface of the lens frame, are put on a person's head directly.

The goggles according to the present invention being constituted as stated above, a wearer can have a preferable fitted comfortability to his face when wearing it directly on his head M as shown in FIG. 10. When he keeps each of the connection arms 3 overlapping and resting on the front surface 1c of the lens frame 1, each of the connection arms 3 is pulled by the wearing belt 2 and force to lift the goggles up from the his face does not work.

Figure 11:
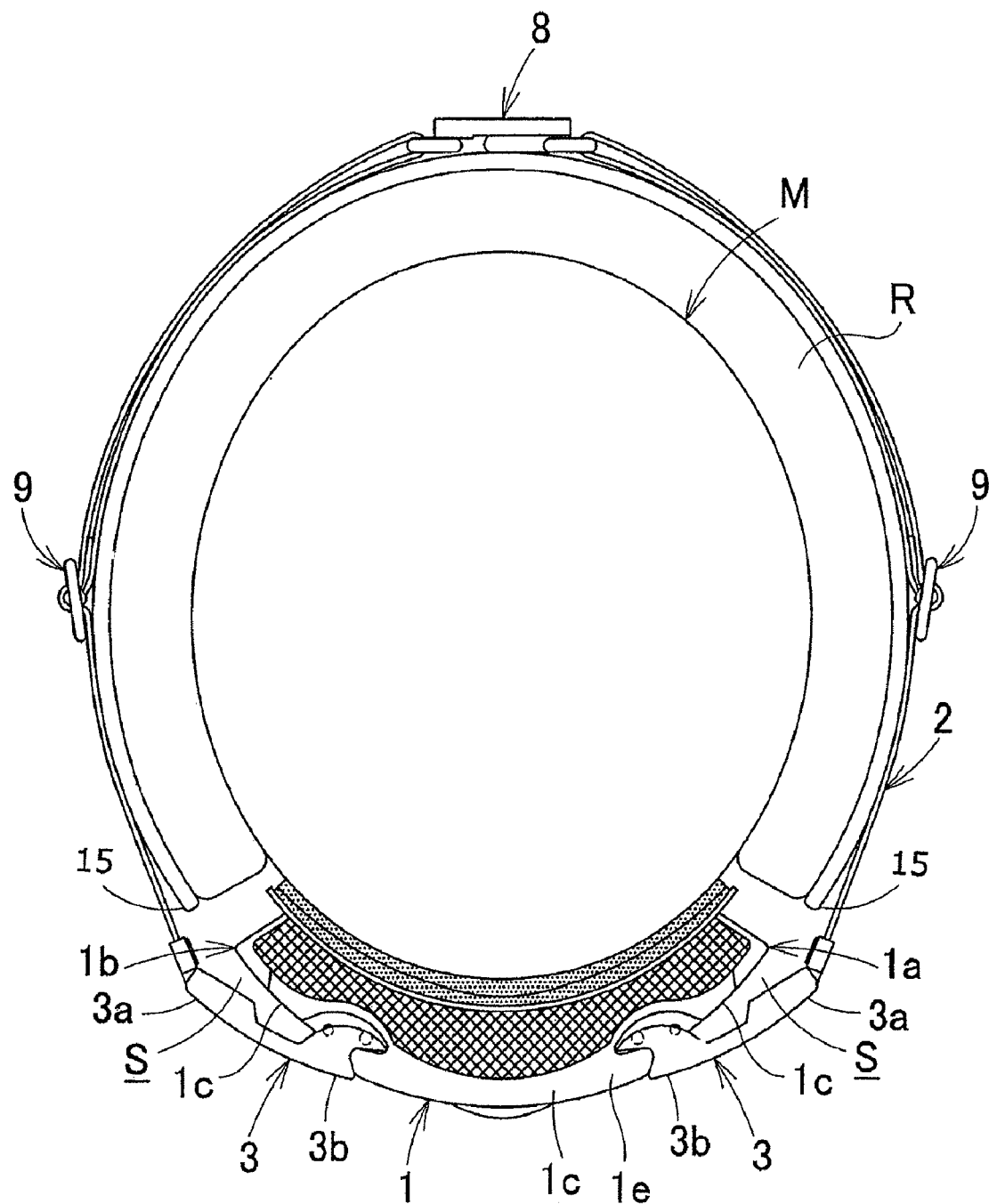
FIG. 11 is an explanatory view showing a state when the goggles of the present invention, in which the connection arms of the goggles are kept staying at a position with a space from the front surface of the lens frame after having moved rotationally on the inner end part from the front surface outwardly, are put on a helmet on the person's head, the helmet having a thick interior liner.
Figure 12:
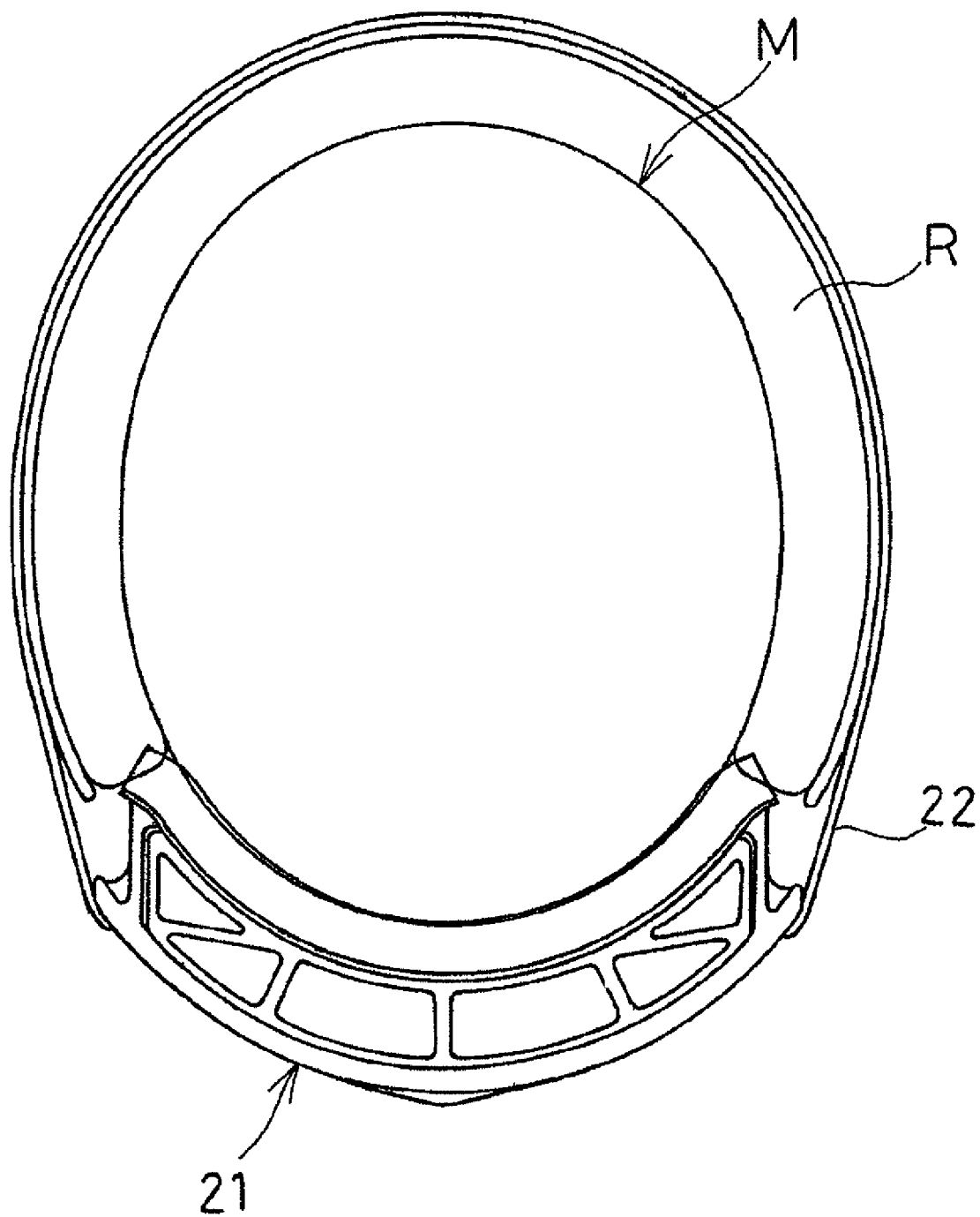
FIG. 12 is an explanatory view showing a state in which a conventional pair of goggles is put on a helmet on a person's head, the helmet having a thick interior liner.
Figure 13:
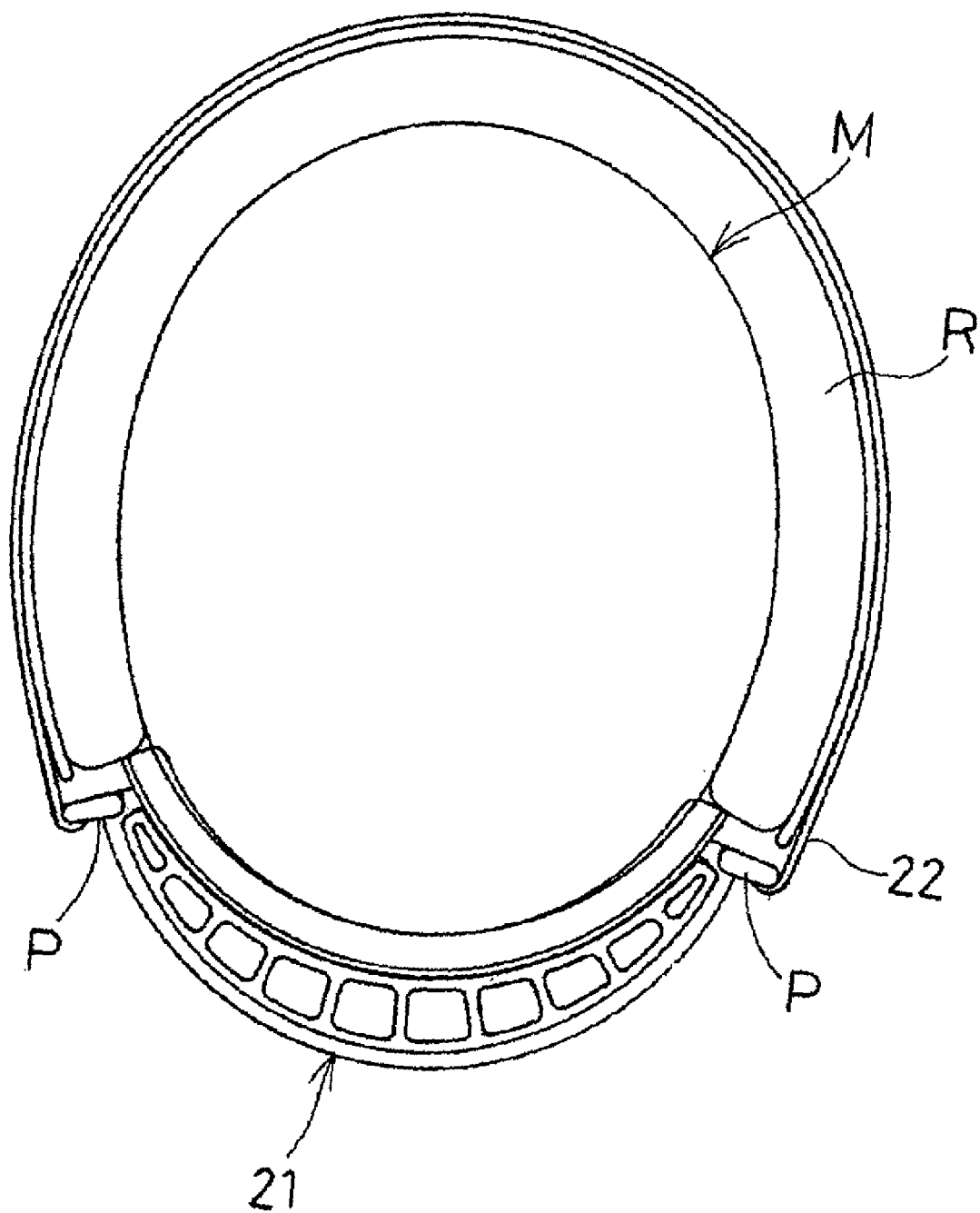
FIG. 13 is an explanatory view showing a state in which another conventional pair of goggles is put on a helmet on a person's head, the helmet having the thick interior liner.
Figure 14:
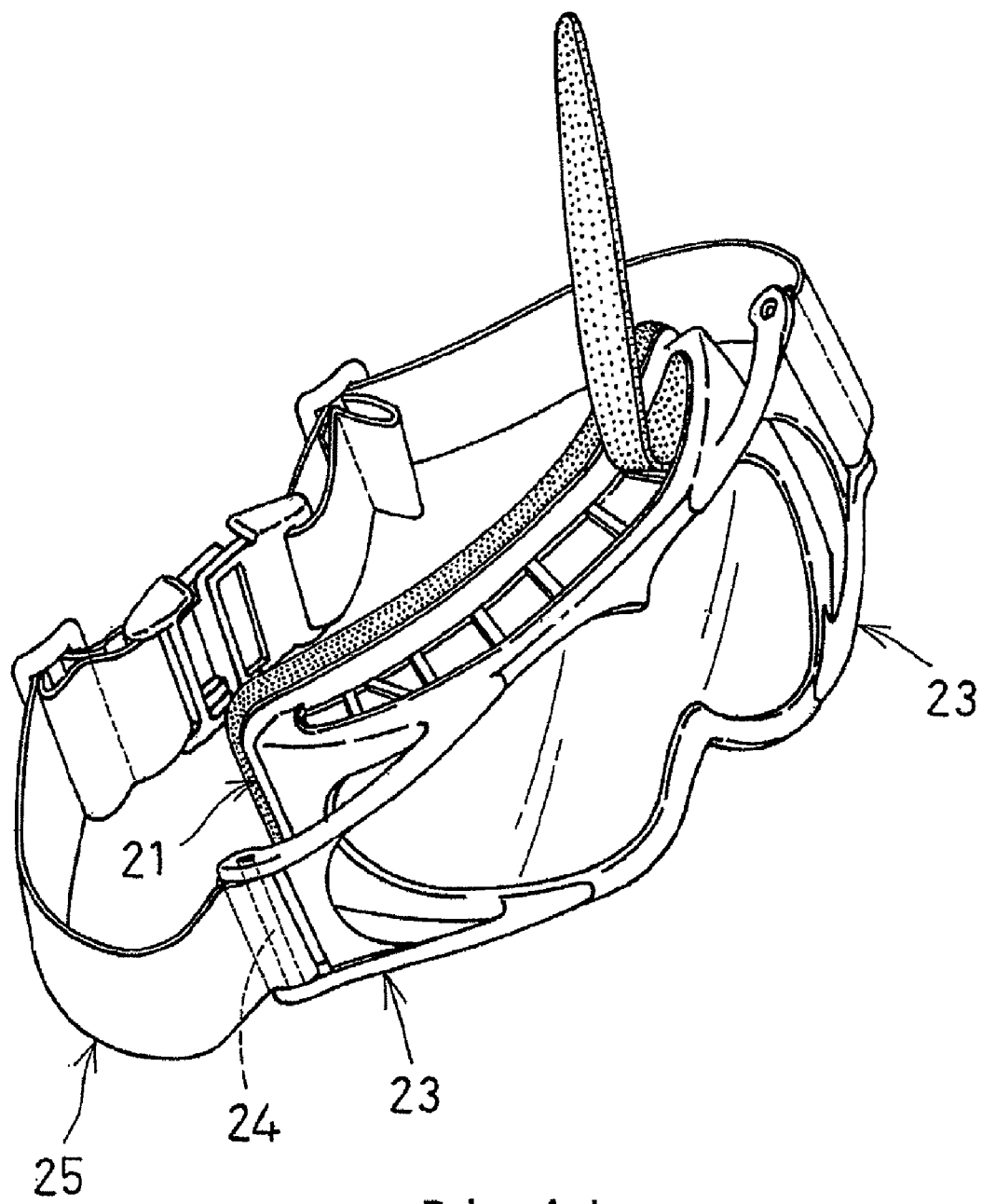
FIG. 14 is a perspective view showing still another example of a conventional pair of goggles.
Figure 15:
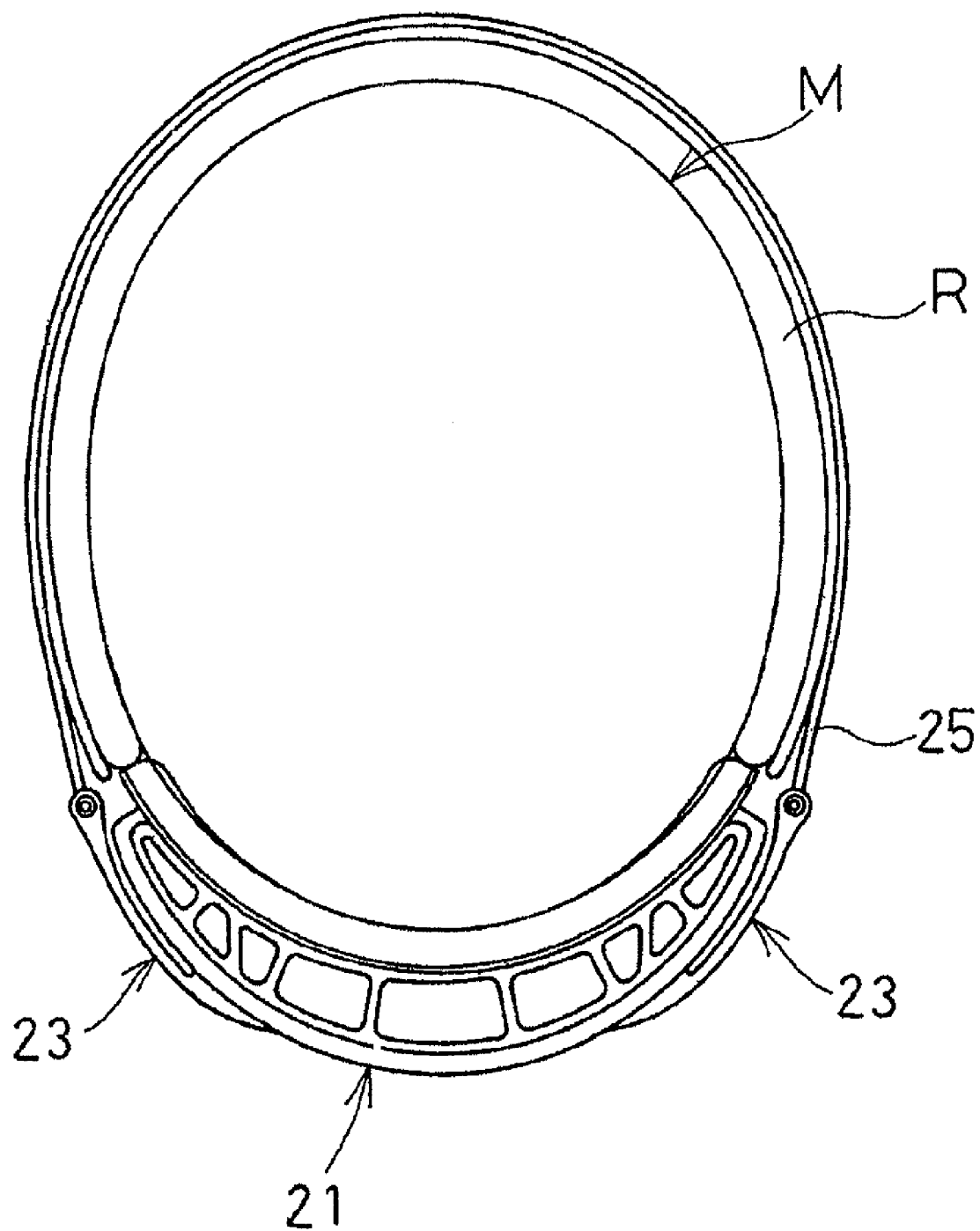
FIG. 15 is an explanatory view showing a state when a person wears the pair of goggles shown in FIG. 14 on a helmet having a thin interior liner.
Figure 16:
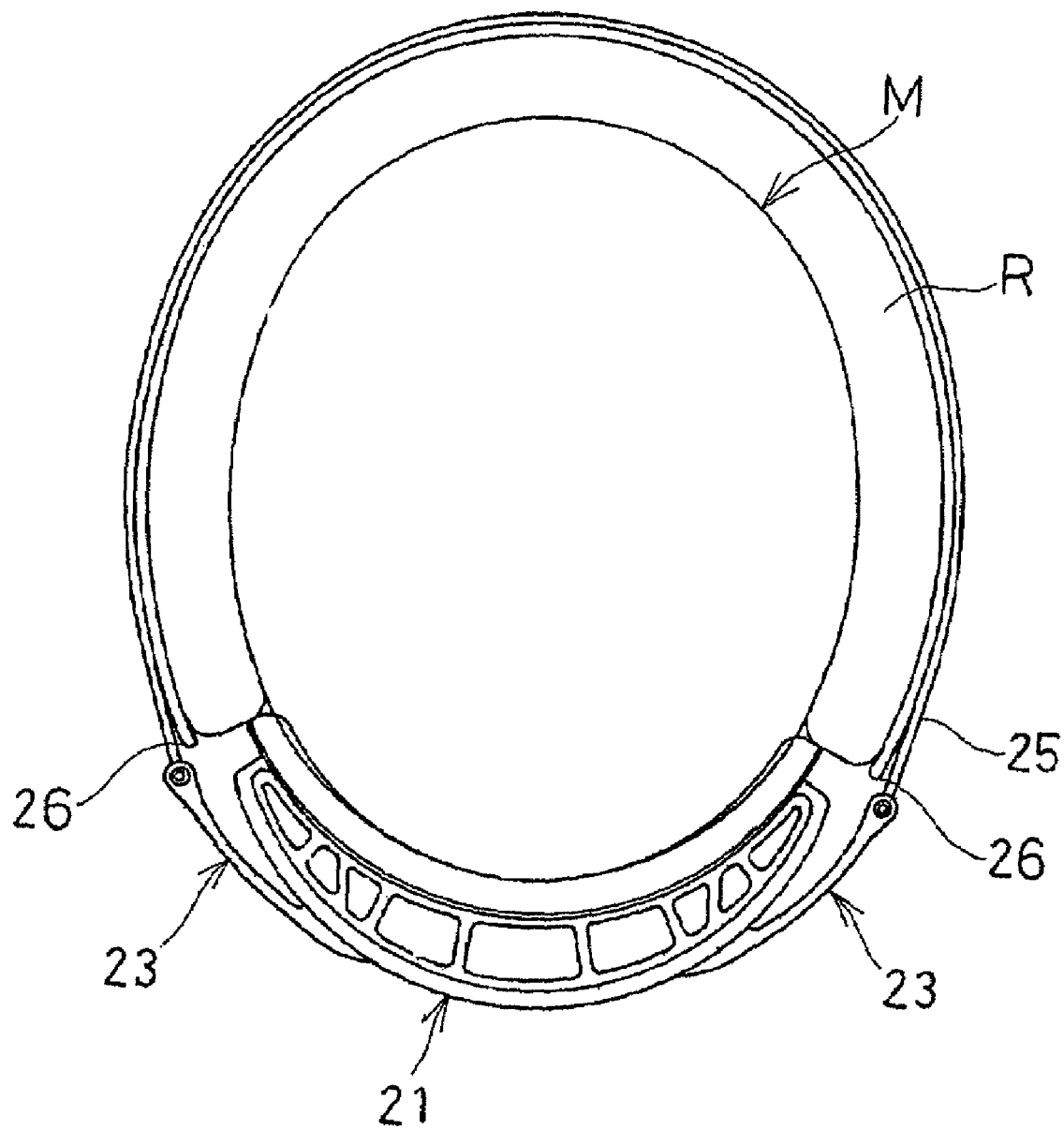
FIG. 16 is an explanatory view showing a state when a person wears the pair of goggles shown in FIG. 14 on a helmet having a thick interior liner.
Figure 17:
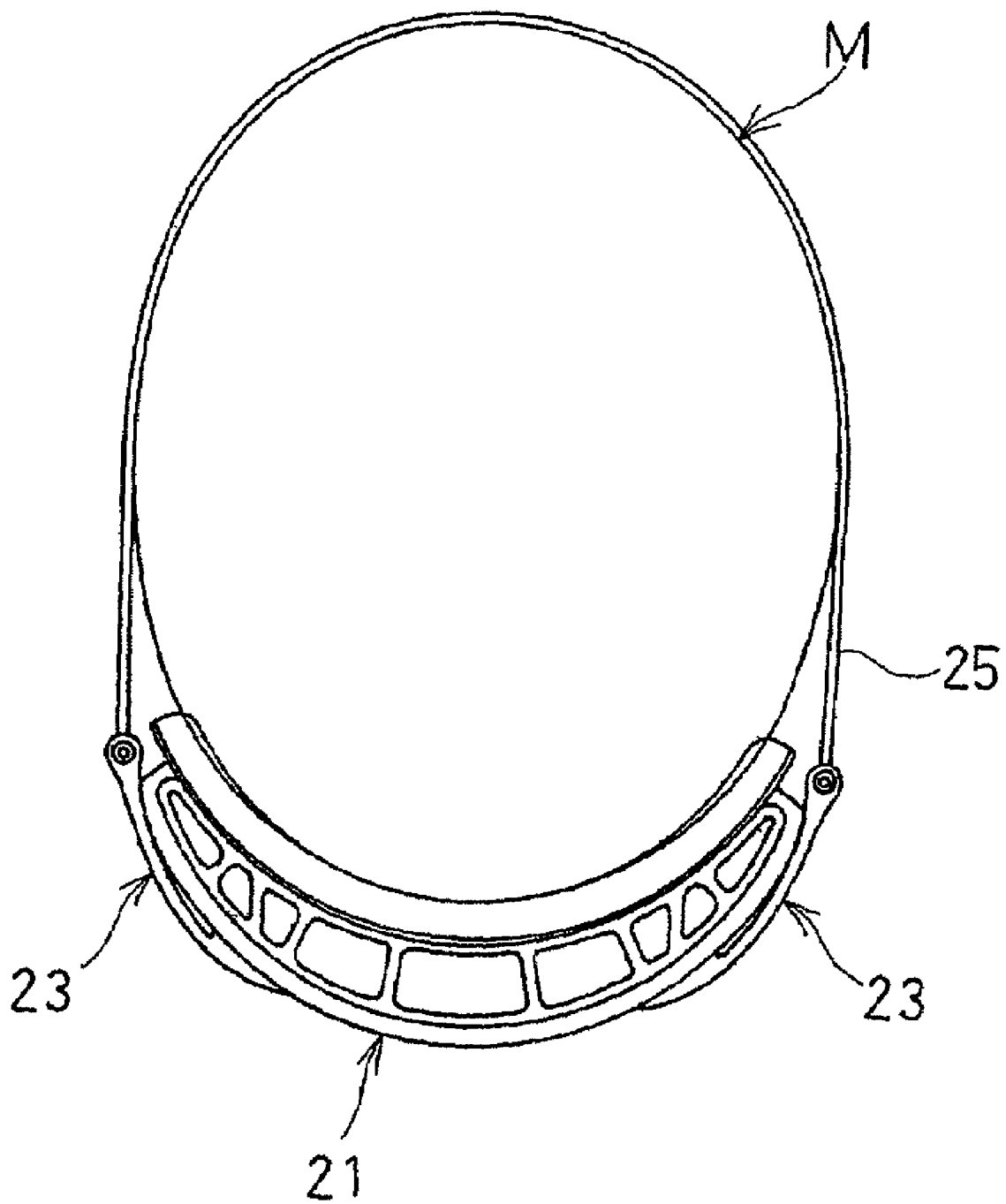
FIG. 17 is an explanatory view showing a state when a person wears the pair of goggles shown in FIG. 14 directly on his head.

Furthermore, in the case where a wearer uses the goggles on a helmet having a thick inner liner R as shown in FIG. 11, when each of the connection arms 3 is kept staying at the position with a space S after having moved rotationally on the side of the inner end part 3b from the side of the front surface 1c of the lens frame 1 outwardly, he can obtain a preferable fitted comfortability to his face. Because the outer end 3a of the connection arm 3 does not abut the opening end 15 of a thick inner liner R, the connection arm 3 is pulled by the wearing belt 2 and force to lift the goggles up from his face does not work.

Therefore, the goggles according to the present invention can provide a suitable fitted comfortability to a wearer's face regardless of whether he uses a helmet or not and regardless of the thickness of the inner liner.

Since the goggles according to the present invention has the structure stated above, a manufacturer of goggles can make the goggles to be used not only when using no helmet where the connection arms 3 are kept overlapping and resting on the front surface 1c of the lens frame 1, but also when using a helmet where the connection arms 3 are kept staying at a position with a space S after having moved rotationally on the side of the inner end part 32 from the side of the front surface 1c of the lens frame 1.

Therefore, according to the goggles of the present invention, by producing one type for goggles, goggle manufacturers can sell them as two types of goggles: one for use on a helmet and the other for use without a helmet, which results in reducing development and production cost.

What is claimed is:

1. Goggles comprising a lens frame and connection arms for a wearing belt, the arms being provided respectively at right and left parts on a side of a front surface of the lens frame, wherein each of the connection arms is kept selectively in one of states that the arm overlaps and rests on the front surface of the lens frame and that the arm stays at a position with a space from the front surface of the lens frame after having moved rotationally on its inner end from the front surface of the lens frame outwardly, further comprising a pivot hole, an engagement hole and an abutment part on each of upper and lower parts on the right and left parts of the side of the front surface of the lens frame, and a pivot part, an engagement part and an abutting part on the inner end part of each of the connection arms, wherein the pivot part of the connection arm is pivotally supported in the pivot hole of the lens frame, and the engagement part of the connection arm is engaged with the engagement hole of the lens frame, so as to keep each of the connection arms in the state that the connection arm overlaps and rests on the front surface of the lens frame.

2. The goggles according to claim 1, wherein the pivot hole of the lens frame penetrates the lens frame, and the connection arm has a retaining part at a tip end part of the pivot part to prevent removal from the pivot hole.

3. The goggles according to claim 1 further comprising a recess part each on the upper and lower parts of the right and left parts of the lens frame, wherein the recess part is provided with the pivot hole and the engagement hole of the lens frame and receives the inner end part of the connection arm.

4. The goggles according to claim 1, wherein each of the connection arms protrudes out from the right and left parts of the lens frame.

5. The goggles according to claim 1, wherein each of the connection arms has a rotational angle of a range of 15 to 22 degrees in which the connection arm moves rotationally on the inner end side from the front surface of the lens frame outwardly.

6. The goggles according to claim 1, wherein the lens frame is formed of soft-type elastic synthetic resin and the connection arms are formed of hard-type elastic synthetic resin.

7. Goggles comprising a lens frame and connection arms for a wearing belt, the arms being provided respectively at right and left parts on a side of a front surface of the lens frame, wherein each of the connection arms is kept selectively in one of states that the arm overlaps and rests on the front surface of the lens frame and that the arm stays at a position with a space from the front surface of the lens frame after having moved rotationally on its inner end from the front surface of the lens frame outwardly, further comprising a pivot hole, an engagement hole and an abutment part on each of upper and lower parts on the right and left parts of the side of the front surface of the lens frame, and a pivot part, an engagement part and an abutting part on the inner end part of each of the connection arms, wherein the pivot part of the connection arm is pivotally supported in the pivot hole of the lens frame, the engagement part of the connection arm is engaged with the front surface of the lens frame, and further the abutting part of the connection arm touches the abutment part of the lens frame to be positioned there, so that each of the connection arms is kept in the state that the arm stays there with the space from the front surface of the lens frame after having moved rotationally on the inner end part from the front surface of the lens frame outwardly.

8. The goggles according to claim 7, wherein the pivot hole of the lens frame penetrates the lens frame, and the connection arm has a retaining part at a tip end part of the pivot part to prevent removal from the pivot hole.

9. The goggles according to claim 7 further comprising a recess part each on the upper and lower parts of the right and left parts of the lens frame, wherein the recess part is provided with the pivot hole and the engagement hole of the lens frame and receives the inner end part of the connection arm.

10. The goggles according to claim 7, wherein each of the connection arms protrudes out from the right and left parts of the lens frame.

11. The goggles according to claim 7, wherein each of the connection arms has a rotational angle of a range of 15 to 22 degrees in which the connection arm moves rotationally on the inner end side from the front surface of the lens frame outwardly.

12. The goggles according to claim 7, wherein the lens frame is formed of soft-type elastic synthetic resin and the connection arms are formed of hard-type elastic synthetic resin.

13. Goggles comprising a lens frame and connection arms for a wearing belt, the arms being provided respectively at right and left parts on a side of a front surface of the lens frame, wherein each of the connection arms is kept selectively in one of states that the arm overlaps and rests on the front surface of the lens frame and that the arm stays at a position with a space from the front surface of the lens frame after having moved rotationally on its inner end from the front surface of the lens frame outwardly, further comprising a pivot part, an engagement hole and an abutment part on each of upper and lower parts on the right and left parts of the side of the front surface of the lens frame, and a pivot hole, an engagement part and an abutting part on the inner end part of each of the connection arms, wherein the connection arm is kept selectively one of the states that the pivot hole of the connection arm pivotally supports the pivot part of the lens frame, and the engagement part of the connection arm is engaged with the engagement hole of the lens frame, so as to keep each of the connection arms in the state that the arm overlaps and rests on the front surface of the lens frame, and that the pivot hole of the connection arm pivotally supports the pivot part of the lens frame, the engagement part of the connection arm is engaged with the front surface of the lens frame, and further the abutting part of the connection arm touches the abutment part of the lens frame to be positioned there, so that each of the connection arms is kept in the state that the arm stays there with the space from the front surface of the lens frame after having moved rotationally on the inner end part from the front surface of the lens frame outwardly.

14. The goggles according to claim 13, wherein the pivot hole of the connection arm penetrates the connection arm, and the lens frame has a retaining part at a tip end part of the pivot part to prevent from removal from the pivot hole.

15. The goggles according to claim 13 further comprising a recess part each on the upper and lower parts of the right and left parts of the lens frame, wherein the recess part is provided with the pivot part and the engagement hole of the lens frame and receives the inner end part of the connection arm.

16. The goggles according to claim 13, wherein each of the connection arms protrudes out from the right and left parts of the lens frame.

17. The goggles according to claim 13, wherein each of the connection arms has a rotational angle of a range of 15 to 22 degrees in which the connection arm moves rotationally on the inner end side from the front surface of the lens frame outwardly.

18. The goggles according to claim 13, wherein the lens frame is formed of soft-type elastic synthetic resin and the connection arms are formed of hard-type elastic synthetic resin.

* * * * *

UNITED STATES PATENT AND TRADEMARK OFFICE
CERTIFICATE OF CORRECTION

| | | |
|---|---|---|
| PATENT NO. | : 7,895,679 B2 | |
| APPLICATION NO. | : 12/033919 | |
| DATED | : March 1, 2011 | |
| INVENTOR(S) | : Takeshi et al. | |

It is certified that error appears in the above-identified patent and that said Letters Patent is hereby corrected as shown below:

Title Page, Item (73) Assignee
    Delete "Yamamoto Kogaku Ltd." and insert -- Yamamoto Kogaku Co., Ltd. --

Signed and Sealed this
Twentieth Day of September, 2011

David J. Kappos
*Director of the United States Patent and Trademark Office*